United States Patent [19]

Flynn et al.

[11] Patent Number: 4,973,585

[45] Date of Patent: Nov. 27, 1990

[54] TRICYCLIC LACTAMS ACTIVE AS ANTIHYPERTENSIVE AGENTS

[75] Inventors: Gary A. Flynn; Douglas W. Beight, both of Cincinnati, Ohio

[73] Assignee: Merrell Dow Pharmaceuticals, Cincinnati, Ohio

[21] Appl. No.: 352,675

[22] Filed: May 10, 1989

Related U.S. Application Data

[63] Continuation of Ser. No. 111,838, Oct. 21, 1987, abandoned, which is a continuation-in-part of Ser. No. 47,872, May 14, 1987, which is a continuation-in-part of Ser. No. 873,754, Jun. 13, 1986, abandoned.

[51] Int. Cl.$^5$ .................... C07D 513/04; A61K 31/55
[52] U.S. Cl. .................................. 514/214; 540/521; 540/522; 540/523
[58] Field of Search ...................... 540/521, 522, 523; 514/214

[56] References Cited

U.S. PATENT DOCUMENTS 4,584,294  4/1986  Ruyle .................................. 514/214

OTHER PUBLICATIONS

P. R. Andrews et al., "Conformational Analysis and Active Site Moddeling of Angiotensin–Converting Enzyme Inhibitors", *J. Med. Chem.*, 28, 393–399, 1985.

*Primary Examiner*—Robert T. Bond
*Attorney Agent or Firm*—William J. Stein

[57] ABSTRACT

This invention relates to derivatives of fused bicyclic or tricyclic lactams, to the intermediates and processes useful for their preparation and to their pharmacological effect in inhibiting the angiotensin converting enzyme and to their end-use application in the treatment of hypertension.

21 Claims, No Drawings

TRICYCLIC LACTAMS ACTIVE AS ANTIHYPERTENSIVE AGENTS

CROSS-REFERENCE TO RELATED APPLICATION

This is a continuation, of application Ser. No. 111,838, filed Oct. 21, 1987 abandoned, which is a continuation-in-part of U.S. Ser. No. 47,872 14, 1987, abandoned which is a continuation-in-part of U.S. Ser. No. 873,754, filed June 13, 1986, now abandoned.

This invention relates to derivatives of fused bicyclic or tricyclic lactams, to the intermediates and processes useful for their preparation, to their pharmacological effect in inhibiting the angiotensin converting enzyme, and to their end-use application in the treatment of hypertension. In particular this invention relates to fused bicyclic or tricyclic lactams of the formula

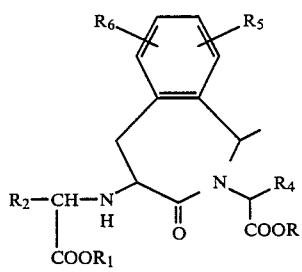

and the pharmaceutically acceptable salts thereof wherein R and $R_1$ each are independently
(a) hydrogen;
(b) $C_1$-$C_6$ alkyl;
(c) substituted $C_1$-$C_6$ alkyl wherein the substituents are hydroxy, $C_1$-$C_4$ alkyloxy and di-$C_1$-$C_4$ alkylamino;
(d) $C_6$ to $C_{12}$ aryl;
(e) substituted $C_6$ to $C_{12}$ aryl wherein the substituents are $C_1$-$C_6$ alkyl, halo (F, Cl, Br, I), and $C_1$-$C_4$ alkyloxy;
(f) hetero ($C_4$ to $C_9$) aryl wherein the heteroatom can be one of O, N or S;
(g) substituted hetero ($C_4$ to $C_9$) aryl wherein the heteroatom can be one of O, N or S and the substituents are $C_1$-$C_6$ alkyl, halo (F, Br, Cl, I) and $C_1$-$C_4$ alkyloxy; or
(h) benzyl, diphenylmethyl, or triphenylmethyl;
$R_2$ is
(a) hydrogen;
(b) $C_1$-$C_8$ straight or branched alkyl;
(c) $C_2$-$C_8$ straight or branched alkenyl;
(d) $C_2$-$C_8$ straight or branched alkynyl;
(e) $C_3C_{10}$cycloalkyl;
(f) $C_6$ or $C_{10}$ aryl ($C_1$-$C_4$) alkyl;
(g) substituted $C_1$-$C_8$ alkyl which can optionally contain an O, S, S=O, O=S=O, C=O, CON(R)$_2$, SO$_2$N(R)$_2$, NRCO$_2$, NRCON(R)$_2$, OCONC(R)$_2$, NRCOOR or —N(R)$_2$ group wherein R is as defined above, and wherein there can be 1-3 substituents selected from halo (F, Br, Cl, I), carboxamido, $C_1$-$C_4$ alkoxy, carbonyl, mercapto, amino, and R wherein R is as defined above;
$R_3$ is H, $C_1$-$C_{12}$ alkyl, phenyl or benzyl;
$R_4$ is H, $C_1$-$C_{12}$ alkyl, phenyl, benzyl or the residue of a natural amino acid, and $R_3$ and $R_4$ taken together with the carbon atoms to which they are attached form a 6 to 8 membered fused ring moiety, optionally having a sulfur or oxygen atom in said ring;
$R_5$ and $R_6$ each are independently
(a) hydrogen;
(b) halo (F, Br, Cl, I);
(c) $C_1$-$C_6$ alkyl;
(d) $C_1$-$C_6$ alkyloxy; or
(e) hydroxy.

The $C_1$-$C_6$ alkyl groups are represented by such groups as, for example, methyl, ethyl, vinyl, propargyl, butenyl, isobutyl, and the like. The $C_3$-$C_{10}$ cycloalkyl groups include, for example, cyclobutyl, cyclopentyl, cyclohexyl, and the like. The $C_6$ to $C_{12}$ aryl groups include phenyl, naphthyl, indenyl, biphenyl and benzofused cycloalkyl groups such as, for example, indanyl and 1,2,3,4,-tetrahydronaphthyl. The $C_4$ to $C_9$ heteroaryl groups include such compounds as, for example, pyridyl, thienyl, furyl, imidazolyl and thiazolyl as well as any bicyclic group in which any of the above heterocyclic rings is fused to another aromatic or heterocyclic ring such as, for example, indolyl, quinolinyl, isoquinolinyl, benzimidazolyl, 1,5-naphthyridyl and quinoxalinyl.

Preferred compounds are those compounds wherein R is hydrogen or $C_1$-$C_6$ alkyl; $R_1$ is hydrogen or $C_1$-$C_6$ alkyl, the preferred alkyl radical being ethyl; $R_2$ is $C_6$ aryl ($C_1$-$C_4$) alkyl, most preferably phenethyl; $R_5$ and $R_6$ are both independently hydrogen or $C_{1-6}$ alkoxy or represent monohydroxy or dihydroxy substituents on the benzenoid moiety; and $R_3$ and $R_4$ together with the atoms to which they are attached form a 6-, 7-, or 8-membered ring. For example, to form a 6 membered ring, together $R_3$ and $R_4$ are preferably —CH$_2$-CH$_2$-CH$_2$—, —CH$_2$—S—CH$_2$—, or —CH$_2$—O—CH$_2$—; to form a 7 membered ring, together $R_3$ and $R_4$ are preferably —CH$_2$—(CH$_2$)$_2$—CH$_2$—; and to form an 8 membered ring, together $R_3$ and $R_4$ preferably are —CH$_2$—(CH$_2$)$_3$—CH$_2$—. The most preferred tricyclic compounds are those wherein $R_3$ and $R_4$ together with the atoms to which they are attached form a 6 membered ring.

The most preferred compounds are those having the diastereomeric configuration represented by the structure:

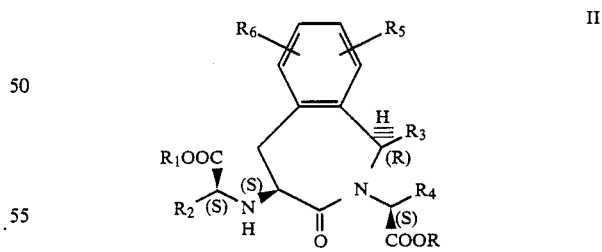

wherein R, $R_1$, $R_2$, $R_3$, $R_4$, $R_5$ and $R_6$ are defined as in Formula I, and wherein the preferred R groups are as noted above, although all of the enantiomeric isomers and diastereomeric isomers and mixtures thereof are within the scope of this invention. The separation of such mixtures may be effected by standard techniques known in the art.

Illustrative examples of compounds of this invention include those compounds of Formula I with the specific values for R, $R_1$, $R_2$, $R_3$, $R_4$, $R_5$ and $R_6$ being in accordance with the following Table I and wherein $R_3$ and $R_4$ taken together with the atoms to which they are attached form a ring.

TABLE I

| R | $R_1$ | $R_2$ | $R_3$–$R_4$ | $R_5$ | $R_6$ |
|---|---|---|---|---|---|
| H | Et | Phenethyl | —(CH$_2$)$_3$— | H | H |
| H | Et | Phenethyl | —(CH$_2$)$_3$— | OH | H |
| H | Et | Phenethyl | —(CH$_2$)$_3$— | OH | OH |
| H | Et | Phenethyl | —CH$_2$—S—CH$_2$— | H | H |
| H | Et | Phenethyl | —CH$_2$—O—CH$_2$— | H | H |
| H | Et | Phenethyl | —CH$_2$—S—CH$_2$— | OH | H |
| H | Et | Phenethyl | —CH$_2$—S—CH$_2$— | OH | OH |
| H | Et | Phenethyl | —(CH$_2$)$_3$— | OH | H |
| H | Et | Phenethyl | —(CH$_2$)$_3$— | OH | OH |
| H | H | Phenethyl | —(CH$_2$)$_3$— | H | H |
| H | H | Phenethyl | —(CH$_2$)$_3$— | OCH$_3$ | H |
| H | H | Phenethyl | —(CH$_2$)$_3$— | OCH$_3$ | OCH$_3$ |
| H | H | Phenethyl | —(CH$_2$)$_3$— | OH | H |
| H | H | Phenethyl | —(CH$_2$)$_3$— | OH | OH |
| H | Et | Pyridylethyl | —(CH$_2$)$_3$— | H | H |
| H | H | Pyridylethyl | —(CH$_2$)$_3$— | H | H |
| Et | Et | Phenethyl | —(CH$_2$)$_3$— | H | H |
| Benzyl | Et | Phenethyl | —(CH$_2$)$_3$— | H | H |
| Diphenyl-methyl | Et | Phenethyl | —(CH$_2$)$_3$— | H | H |
| H | Et | Phenylthio-methyl | —(CH$_2$)$_3$— | H | H |
| H | H | Phenethyl | —(CH$_2$)$_5$— | OH | H |
| Et | Et | Phenethyl | —(CH$_2$)$_4$— | H | H |

Further illustrative examples of compounds of this invention include those compounds of Formula I with specific values for R, $R_1$, $R_2$, $R_3$, $R_4$, $R_5$ and $R_6$ being in accordance with the following Table II, where $R_3$ and $R_4$ are not taken together.

TABLE II

| R | $R_1$ | $R_2$ | $R_3$ | $R_4$ | $R_5$ | $R_6$ |
|---|---|---|---|---|---|---|
| H | Et | Phenethyl | H | isopropyl | H | H |
| H | Et | Phenethyl | H | isopropyl | OH | H |
| H | Et | Phenethyl | H | isopropyl | OH | OH |
| H | H | Phenethyl | H | isopropyl | H | H |
| H | Et | Phenethyl | H | CH$_3$ | H | H |
| H | Et | Phenethyl | H | H | H | H |
| H | Et | Phenethyl | Phenyl | H | H | H |
| H | Et | Phenethyl | Phenyl | CH$_3$ | H | H |
| H | Et | Phenethyl | Phenyl | isopropyl | H | H |

The preferred method for the preparation of the preferred R-triflate may be effected by the process of our co-pending U.S. patent application Ser. No. 7/019,102, filed Feb. 26, 1987, said application bearing the title "Process for Making and Isolating (R)-2-Hydroxy-4-Phenylbutyric Acid and Esters."

In preparation of the compounds of this invention, it is generally preferred to initiate the sequence of reaction steps by utilizing an appropriate N-protected arylalanine which, when converted to its acid chloride, is coupled with an appropriate $R_3$ and/or $R_4$ substituted amine, according to the well-known principles of the Schott-Baumann reaction. Depending on whether or not the desired final product contains an additional fused ring with the benzazepin-2-one moiety, (i.e., whether or not $R_3$ and $R_4$, together with the atoms to which they are attached, form, for example, a pyridobenzazepin-2-one moiety,) different intermediates and processes will be employed. In either event, however, before the nitrogen atom which is attached to the 3-position of the benzazepin-2-one moiety is subjected to coupling procedures, the appropriate $R_3$ and $R_4$ bearing imtermediates are subjected to a Friedel-Crafts cyclization reaction. Following the cyclization, the N-protecting group, (e.g., a phthalimido moiety) is removed and the nitrogen atom is subjected to coupling procedures known in the art to produce the desired $R_1$, $R_2$ bearing compounds of formula I.

Reaction Scheme A depicts the synthetic route utilized in those instances wherein the $R_3$ and $R_4$ substituents do not form an additional fused ring with the benzazepin-2-one moiety. Acid chloride derivatives of the N-protected L-arylalanines (III) are coupled with an appropriately $R_4$ substituted amino acid (IV), according to the Schott-Baumann reaction, wherein the reactants are coupled in the presence of sodium carbonate/acetone and water, preferably at room temperature, and then subjected to a finishing acidification step. The product obtained thereby (V) is reacted with an $R_3$ bearing aldehyde by refluxing the reactant in the presence of p-toluenesulfonic acid in an azeotropic-facilitating solvent, (e.g., benzene, toluene, chloroform, and the like) to produce an intermediate oxazolinone (VI) which, when treated with a Lewis acid such as polyphosphoric acid, CF$_3$SO$_3$H or its trimethylsilyl ester to protonate the carbonyl, forms an acyliminium ion intermediate which, in situ, is subjected to the Friedel-Crafts reaction. The acyliminium ion intermediate undergoes Friedel-Crafts cyclization to produce compound VII which is converted to an appropriate alkyl ester (VIII) by standard and well known techniques.

Reaction Scheme A

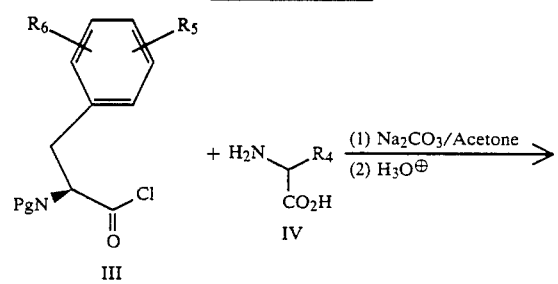

-continued
Reaction Scheme A

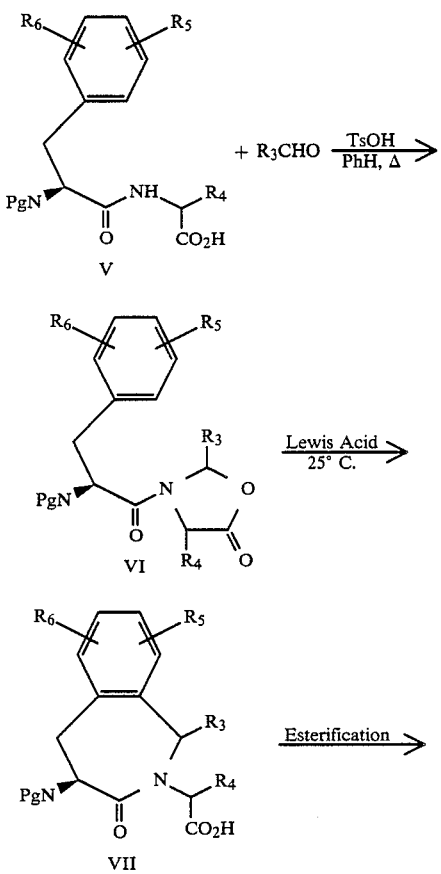

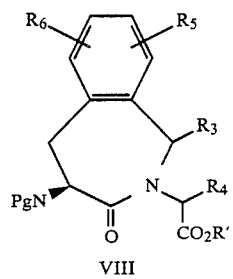

wherein Pg is a N-protecting group (preferably phthalimido); TsOH is p-toluenesulfonic acid; PhH is phenylhydride; $R_3$, $R_4$, $R_5$ and $R_6$ are as defined in Formula I, and R' is as defined for R of Formula I except that it cannot be H. To obtain the preferred final products of Formula I, it is often preferred to prepare esters wherein the R group is selected from group (h).

Reaction Scheme B depicts the synthetic route utilized in those instances when it is desired to prepare compounds wherein $R_3$ and $R_4$ form an additional fused ring with the azepin-2-one ring. Acid chloride derivatives of the N-protected arylalanine (III of Scheme A) are coupled by treatment with an aminovinyl chloride (IXa) or an —OH protected vinyl amino acid (IXb), according to the above described Schott-Baumann reaction, to produce intermediates Xa and Xb respectively. These intermediates are treated with ozone in methylene chloride containing an alcohol at $-78°$ C., quenched with dimethylsulfide and pyridine, and the isolated products are treated with trifluoroacetic acid/methylene chloride at reflux temperatures to produce acylenamines (XIa and XIb) which are then treated with $CF_3SO_3H$ according to the Friedel-Crafts cyclization procedure to produce compounds XIIa and XIIb.

In effecting the Friedel-Crafts cyclization, it is preferred to utilize a Lewis acid chosen from such perfluoroalkyl sulfonic acids as, for example, trifluoromethane sulfonic acid, pentafluoroethane sulfonic acid and heptafluoropropane sulfonic acid.

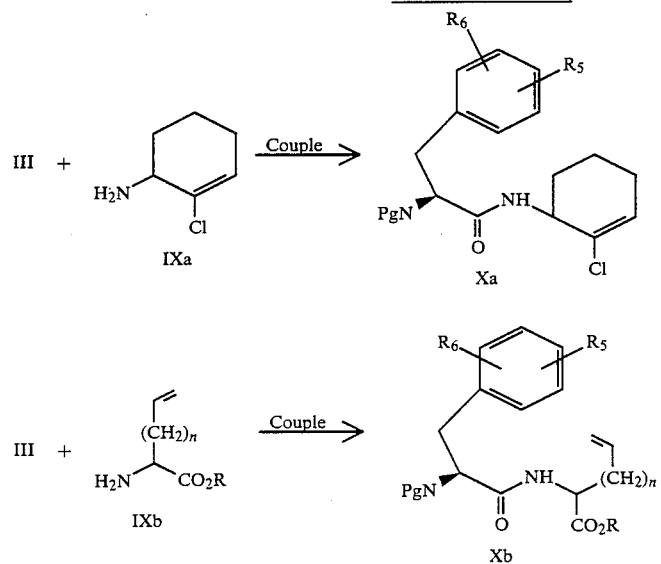

-continued
Reaction Scheme B

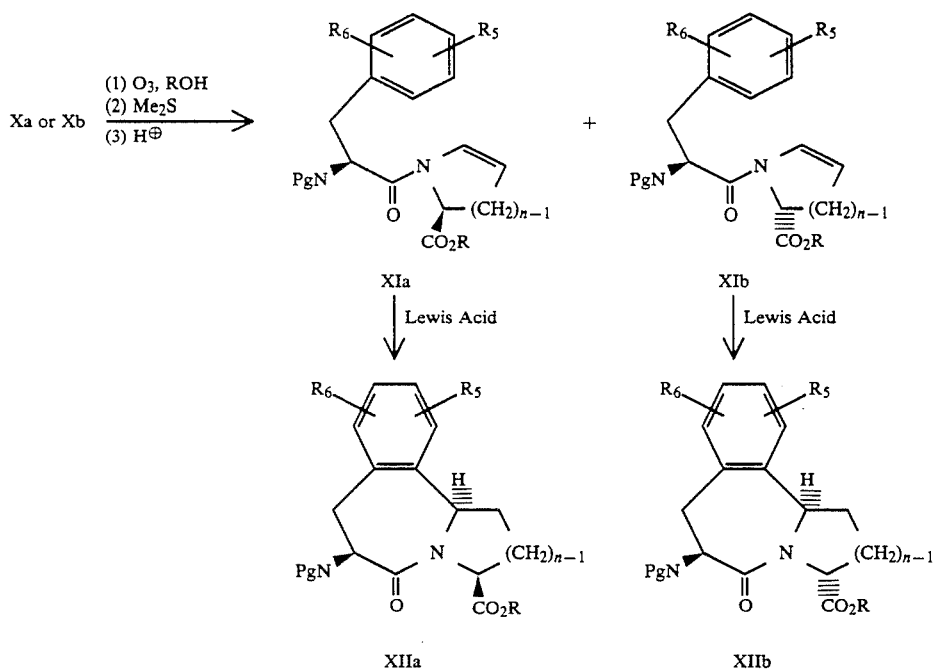

wherein R, $R_5$, and $R_6$, are as defined in Formula I, Pg is a N-protecting group (preferably phthalimido), and n is the integer 3, 4 or 5.

In those instances when it is desired to produce compounds wherein $R_3$ and $R_4$ produce a fused ring bearing a sulfur or oxygen in that ring, such compounds are prepared according to Reaction Scheme C. The N-protected phenylalanyl serine ester (XIII), prepared from the coupling of an acid chloride of structure III with an ester of L-serine, is converted (in situ), to its mesylate and then eliminated to give the dehydroalanine (XIV) by treatment with methane sulfonyl chloride in triethylamine in an inert solvent such as dichloromethane. Conjugate addition of $HXCH_2CH(OEt)_2$ (XV) with the dehydroalanine intermediate (XIV) gives a Michael adduct (XVI) which is cyclized to acylenamine (XVII) by the action of trifluoroacetic acid in dichloromethane. Final cyclization to (XVIII) is effected by the above described Friedel-Crafts reaction.

Reaction Scheme C

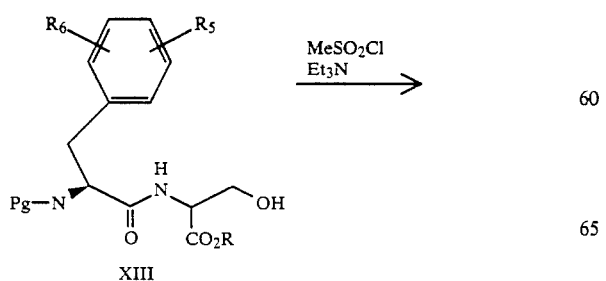

-continued
Reaction Scheme C

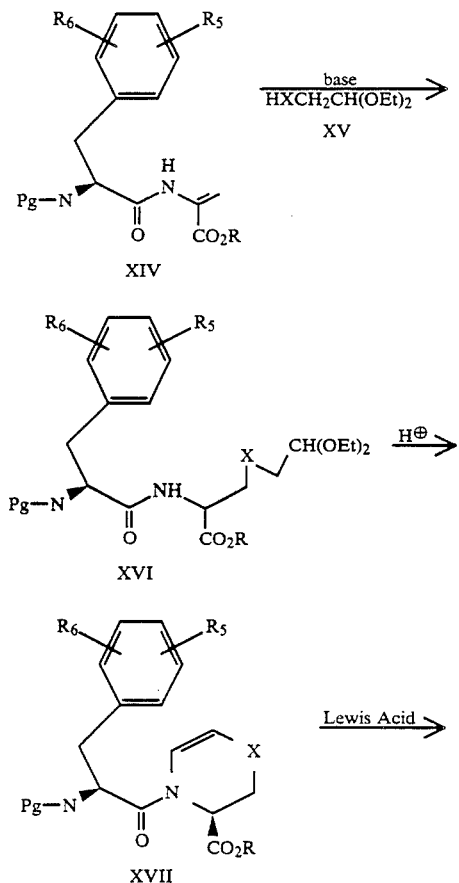

-continued
Reaction Scheme C

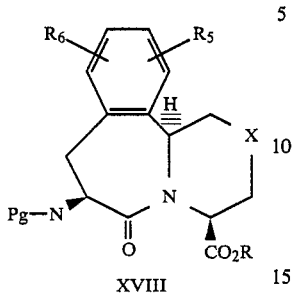

XVIII wherein Pg is an N-protecting group (preferably phthalimido), R, $R_5$, $R_6$ are as defined in I, and X is S or O.

Alternately, Reaction Scheme D depicts how, in the specific instance wherein X of the fused ring structure for $R_3$ and $R_4$ is sulfur, the intermediates XVIa may be prepared by alkylation of L-cysteine ethyl ester (XIX) with bromoacetaldehyde diethyl acetyl and sodium iodide, is DMF, and catalyzed with a suitable base such as triethylamine or sodium hydride. The resulting free amine (XX) is coupled to an N-protected L-phenylalanine (XXI) by action of standard coupling reagents such as N-carbethoxy-2-ethoxy-1,2-dihydroquinoline, to give the intermediate (XVIa) which are cyclized according to standard Lewis acid Friedel-Crafts cyclization procedures as described above.

Reaction Scheme D

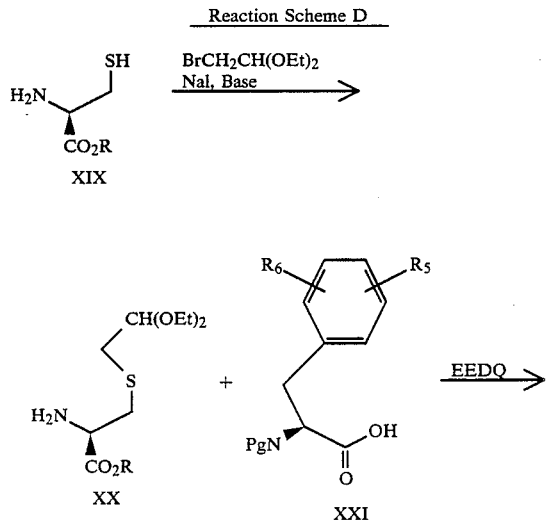

-continued
Reaction Scheme D

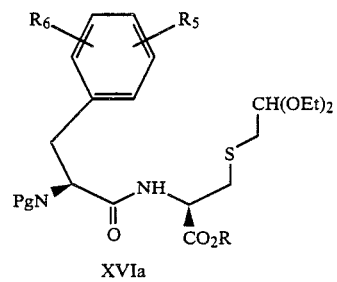

XVIa wherein R, $R_5$, $R_6$ and Pg are as previously defined, and EEDQ is N-carbethoxy-2-ethoxy-1,2-di-hydroquinone.

When utilizing Reaction Schemes A, B, C and D to prepare a fused lactam by a Friedel-Crafts cyclization procedure, the Lewis acid utilized is most preferably a perfluoroalkyl sulfonic acid.

Once the fused lactams VIII, XIIa, XIIb and XVIII have been prepared, the N-protecting group is removed so that the appropriate side chain may be coupled to the free amine. This deprotection may be effected by standard and well known procedures. In the instance wherein the protecting group is phthaloyl, it is convenient to remove the phthalimido moiety by reaction with hydrazine hydrate by techniques well-known in the art.

Although all of the diastereomeric forms of the fused lactams are contemplated, the preferred deprotected fused lactams are as depicted by the following structure

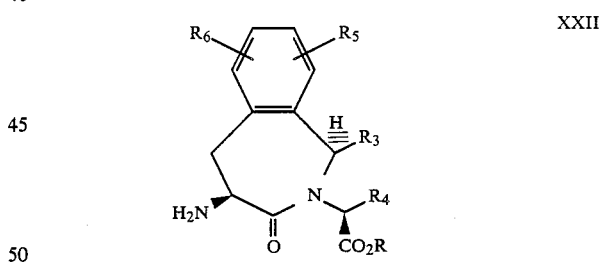

XXII wherein all R groups are as defined in Formula I.

In cases where the R group of XXII is hydrogen, these compounds may be prepared from their corresponding esters, i.e. R=R', by the action of an hydroxide ion such as lithium hydroxide in a suitable protic solvent such as ethyl alcohol.

It is also to be noted that although the preferred diastereomeric forms of the fused lactams are depicted in formulae XXIII, XXVI, and XXVII, it should be understood that all other diastereomeric forms may be prepared by analogous techniques.

Although any known procedure generally used for such couplings may be utilized, the preferred methods for such couplings are shown in Reaction Scheme E.

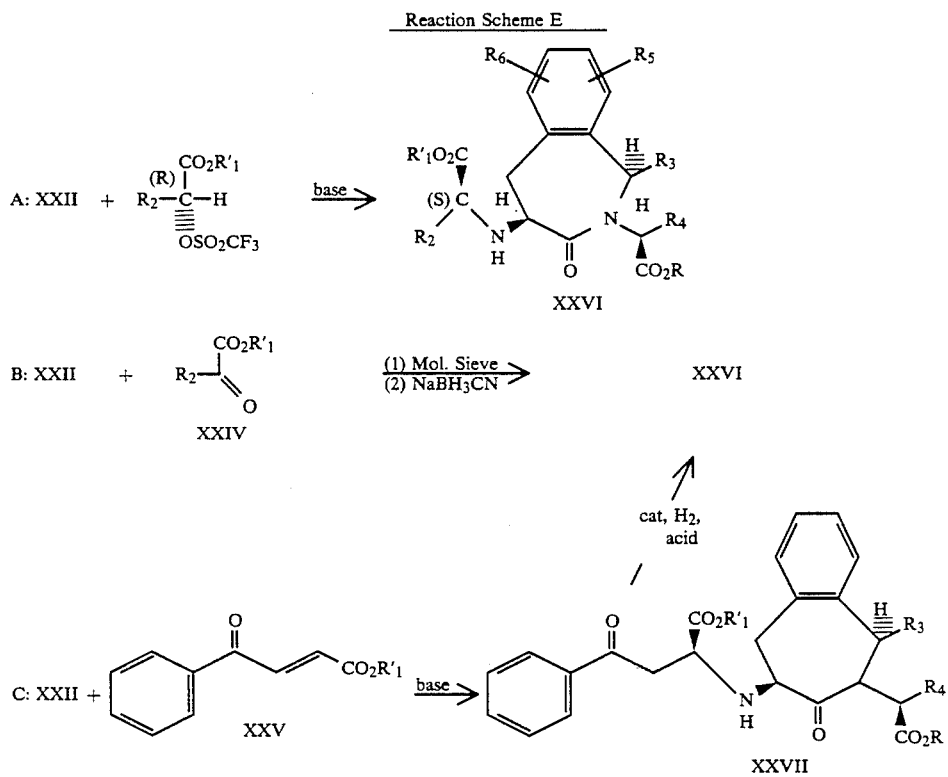

Reaction Scheme E wherein $R'_1$ is the same as $R_1$ of Formula 1 except it cannot be H, and all other R groups are as defined in Formula 1.

Method A of Scheme E entails the displacement reaction with a (R) triflate (XXIII) wherein the fused lactams are contacted with the triflate in the presence of a base such as, e.g., triethylamine, but more preferably in the presence of a "proton sponge", such as, for instance, 1,8-bis-(dimethylamino)-naphthalene, to produce compound XXVI.

Method B entails the use of a keto ester (XXIV) in ethanol or other alcoholic solvent, with a molecular sieve or other dehydrating agent, to form a Schiff's base which is reduced to compound XXVI, preferably using sodium cyanborohydride.

Method C entails a 1,4-Michael addition reaction with an ethyl-4-oxo-4-arylcrotonate (XXV). The ketone oxygen of intermediate XXVII is reduced by catalytic hydrogenation, preferably utilizing a palladium catalyst in the presence of small amounts of sulfuric acid to give compound XXVI. Since a preferred embodiment of compounds of this invention relates to those compounds of Formula I wherein R is H and $R_1$ is other than H (preferably ethyl) certain comments relating to the foregoing coupling procedures of Reaction Scheme E are to be noted, particularly as they relate to the selective hydrolysis of the R ester groups. For example, in general, for the selective hydrolysis of compound XXVI when R is other than hydrogen, it is preferred to prepare esters wherein R is a member of group (h) (that is, benzyl, diphenylmethyl, or triphenylmethyl) because these groups may be selectively hydrolysed with mild acids (for example, by reaction with ethereal hydrochloric acid or with trifluoroacetic acid), or else they may be subjected to catalytic hydrogenolysis. Similarly, as the reduction of the ketonic oxygen (in compound XXVII) will also hydrolyze off the R group of the ester moiety to its corresponding acid, it is also preferred that compounds XXVII have an ester group wherein R is selected from group (h). Also, peculiar to any compound wherein $R_3$ and $R_4$, together with the atoms to which they are attached, form a six membered ring, any R group other than H may be selectively hydrolyzed to its corresponding acid by treatment with a perfluoroalkyl sulfonic acid. Suitable perfluoroalkyl sulfonic acids are trifluoromethane sulfonic acid, pentafluoroethane sulfonic acid and heptafluoropropane sulfonic acid.

The following examples illustrate the techniques and conditions by which the compounds of this invention may be prepared, but they should not be construed to be limiting in any way.

EXAMPLE 1

[2(S)]N-(2-Chloro-2-cyclohexene-1-yl)-1,3-dihydro-1,3-dioxo-2H-isoindole-2-(S)-(phenylmethyl-2-acetamide (Xa)

Step A.
2-(2-Chloro-2-cyclohexen-1-yl)-1H-isoindole-1,3(2H)-dione

A solution of 11.0 g (72.8 mmol) 1,6-dichlorocyclohexene, 20.0 g (108 mmol) potassium phthalimide and 1.0 g (6.0 mmol) potassium iodide in 50 ml dry dimethylformamide was stirred 24 hours at 110° C. under an atmosphere of nitrogen. The reaction mixture was allowed to cool then poured into 30 ml diethyl ether. The dark mixture was filtered then ether and DMF removed in vacuo. The dark crystalline residue was dissolved in ethyl acetate then chromatographed on 500 g flash silica eluting with 10% to 20% ethyl acetate/hexane. Concentration of appropriate fractions followed by recrystallization from ethyl acetate/hexane gave 14.0 g (73.5%) of the desired phthalimide, mp 99°–103° C.

Step B.

A solution of 6.0 g (120 mmol) of hydrazinehydrate and 26.1 g (100 mmol) of N-phthalimido-6-amino-1-chlorocyclohexene in 150 ml methanol was refluxed under $N_2$ for 3 hrs., cooled to 25° C. and allowed to stir for 3 hrs. The mixture was filtered, concentrated, poured into 300 ml 1N HCl, and washed with 200 ml $CH_2Cl_2$. The aqueous layer was basified and extracted with three 500 ml portions of $CH_2Cl_2$. The organics were dried over $MgSO_4$, filtered, and concentrated to give 9.25 g (70 mmol) of crude amine. The neutral extract was concentrated to give 6.0 g of unreacted starting phthalimide. To a stirred solution of 21 g (71 mmol) of phthalimido-L-phenylalanine and 18.5 g (75 mmol) of N-carbethoxy-2-ethoxy-1,2-dihydroquinoline in 200 ml $CH_2Cl_2$ at 25° C. under $N_2$ was added 9.25 g (70 mmol) of the 6-amino-1-chlorocyclohexene in 20 ml $CH_2Cl_2$ over 30 min. After stirring for 18 hours, the reaction mixture was washed with two 200 ml portions of 10% HCl solution, 200 ml sat. $NaHCO_3$ solution, and brine. The organics were dried over $MgSO_4$, filtered and concentrated to give a solid. Recrystallization from $CH_2Cl_2$/hexane gave 26.1 g of a mixture of the desired 2-(S) diastereomeric amides (Xa) which were not separated at this point. (64% overall yield): IR(KBr) 3400, 1775, 1715, 1650, 1530, 1380, cm$^{-1}$; NMR $\delta$1.60 (m,2H), 1.82 (m,2H), 2.05 (m,2H), 3.49 (s,1H), 3.59 (s,1H), 4.60 (m,1H), 5.05 (dd, ½H, $J_a$=10 Hz, $J_b$=2 Hz), 5.17 {dd, ½H, $J_a$=10 Hz, $J_b$=2 Hz), 5.95 (t, 1H, J=7 Hz), 6.45 (m,1H), 7.10 (s,5H), 7.70 (m,4H).

Anal. Calcd. for $C_{23}H_{21}ClN_2O_3$: C,67.56; H,5.18; N,6.85. Found: C,67.40; H,5.30; N,6.80.

EXAMPLE 2

[S(R*,R*)]-1-[2-(1,3-Dihydro-1,3-dioxo-2H-isoindol-2-yl)-1-oxo-3-phenylpropyl]-1,2,3,4-tetrahydro-2-pyridinecarboxylicacid, methyl ester (XIa)

A solution of 12.2 g (30 mmol) of vinyl chloride Xa from Example 1 in 300 ml $CH_2Cl_2$ containing 20 ml absolute methanol was cooled to −70° C. and stirred while a stream of ozone in oxygen (generated by a Welsbach Ozonator) was passed via a glass frit into the solution. When the solution turned blue, excess ozone was removed by passing dry $N_2$. The reaction mixture was treated with 20 ml methyl sulfide and 4 ml pyridine then allowed to gradually warm to 25° C. and stir for 20 hours. The solution was poured into 200 ml 10% HCl solution and the organics were separated, washed well with $H_2O$, dried over $MgSO_4$ and concentrated to give 13.0 g of an amber oil. The crude ozonolysis product was dissolved in 200 ml $CH_2Cl_2$ containing 0.5 ml trifluoroacetic acid and refluxed under $N_2$ for 3 hours. The cooled solution was washed with saturated $NaHCO_3$ solution, dried over $MgSO_4$ and concentrated to give 12.2 g of an amber oil. Preparative HPLC separation using 50% ethyl acteate/hexane (Waters Prep-500 one recycle) gave 4.3 g (10.1 mmol) of each diastereomeric acylenamine XIa and XIb (n=2), (68% overall yield). Isomer XIa was recrystallized from $CH_2Cl_2$/hexane to give a fine white crystalline powder: mp 146°–147° C.; $[\alpha]_D^{Amb}$= −320.1° (C=1.1,CHCl$_3$); IR (KBr) 1770, 1740, 1720, 1670, 1650, 1390, 1220, 722 cm$^{-1}$;NMR $\delta$1.85 (m,2H), 2.30 (m,2H), 3.50 (d, 2H, J=7 Hz), 3.72 (s,3H), 4.71 (m,1H), 5.20 (m,1H), 5.27 (t, 1H, J=7 Hz), 6.45 (d, 1H, J=9 Hz), 7.12 (s,5H), 7.71 (m,4H).

Anal. Calcd. for $C_{23}C_{22}N_2O_5$: C,68.89; H,5.30; N,6.69. Found: C,68.61; H,5.26; N,6.56.

EXAMPLE 3

[4S-(4α,7α,12bβ)]-7-(1,3-Dihydro-1,3-dioxo-2H-isoindo-2-yl)-1,2,3,4,-6,7,8,12b-octahydro-6-oxopyrido[2,1-a][2]benzazepine-4-carboxylic acid, diphenylmethyl ester* (XIIa)

A solution of 4.20 g (10.0 mmol) of desired acylenamine XIa from Example 2 in 20 ml $CH_2Cl_2$ under $N_2$ atmosphere was added to 6 ml $CF_3SO_3H$ with stirring. After stirring at 20° C. for 18 hours, the solution was poured onto ice and extracted into 200 ml ethyl acetate. The organics were washed well with water, dried over $MgSO_4$ and concentrated. The residue was dissolved in $CH_2Cl_2$ and treated with 2.2 g diazodiphenylmethane and allowed to stand for 12 hours. The solution was concentrated and the residue was flash chromatographed on 400 ml silica using 33% ethyl acetate/hexane to give 4.5 g (7.7 mmol, 77% yield) of benzhydrylester XII (R=CHPh$_2$) as a foam. Recrystallization from $CH_2Cl_2$/hexane was slow but gave 4.3 g (75% yield) of pure transparent plates: mp. 156°–157° C.; $[\alpha]_D^{Amb}$= −87.6° C. (c=0.6, CHCl$_3$);IR 1780, 1717, 1643, 1450, 1379 cm$^{-1}$; NMR $\delta$1.8–2.1 (m,4H), 2.38 (m,2H); 3.23 (dd, 1H, $J_a$=18 Hz, $J_b$=16 Hz), 4.38 (dd, 1H, $J_a$=19 Hz. $J_b$=12 Hz), 5.30 (dd, 1H, $J_a$=6 Hz, $J_b$=2 Hz), 5.42 (dd, 1H, $J_a$=6 Hz, $J_b$=4 Hz, 6.05 (dd, 1H, $J_a$=12 Hz, $J_b$=6 Hz), 6.30 (s,1H), 6.61 (d, 1H, J=7 Hz), 6.9–7.4 (m,13 H), 7.75 (m,2H), 7.92 (m,2H). *(A compound of formula XII wherein R is diphenylmethyl and R$_5$ and R$_6$ are hydrogen and n is 3)

Anal. Calcd. for $C_{36}H_{30}N_2O_5$: C,75.77; H,5.30; N,4.91. Found: C,75.79; H,5.46; N,4.77.

EXAMPLE 4

[4S-(4α,7α,12bβ)]-7-(1,3-Dihydro-1,3-dioxo-2H-isoindol-2-yl)-1,2,3,4,6,7,8,-12b-octahydro-6-oxopyrido[1-a][2]benzazepine-4-carboxylic acid, methyl ester Alternatively the cyclization product could be treated with diazomethane to give methyl ester XII from Example 3 (R-CH$_3$) mp 138°–149° C. $[\alpha_D^{Amb}$= −122.4° (c=0.97,EtOH); IR 1778, 1720, 1655, 1620, 1375 cm$^{-1}$, NMR $\delta$1.7–2.2 (m,4H), 2.43 (m,2H), 3.10 (s,3H), 3.44 (dd, 1H, $J_a$=17 Hz, $J_b$=6 Hz), 4.42 (dd, 1H, $J_a$=17 Hz, $J_b$=12 Hz), 5.23 (dd, 1H, $J_a$=6 Hz, $J_b$=2 Hz), 5.47 (dd, 1H, $J_a$=6 Hz, $J_b$=4 Hz), 6.08 (dd, 1H, $J_a$=12 Hz, $J_b$=6 Hz), 7.23 (m,4H), 7.77 (m,2H), 7.89 (m,2H).

Anal. Cacd. for $C_{24}H_{22}N_2O_5$: C,68.89; H,5.30; N,6.69. Found: C,68.98; H,5.83; N,6.63.

EXAMPLE 5

[4α,7α,12bβ)-7-[[1-(Ethoxycarbonyl)-3-phenylpropyl]amino]-1,2,3,4,6,7,8,12b-octahydro-6-oxopyrido[2,1-a][2]benzazepine-4-carboxylic acid, diphenylmethyl ester (IIa)

To a solution of 1.17 g (2.0 mmol) of phthalimide XII from Example 3 (R=CHPh$_2$) in 15 ml methanol was added 2.3 ml 1N hydrazine hydrate solution in methanol and the solution was stirred at 25° C. for 3 days. The solvent was removed in vacuo giving a residue which was dissolved in CHCl$_3$, filtered and concentrated to give the crude amine as a light yellow oil. This crude amine (ca. 2.0 mmol) was dissolved in 6 ml CH$_2$Cl$_2$ under N$_2$ at 25° C. and treated with 545 mg (2.5 mmol) 1,8,-bis-(dimethylamino)naphthalene followed by 850 mg (2.5 mmol) of (R)-ethyl 4-phenyl-2trifluoromethanesulfonyloxybutanoate (XXIII). The solution was stirred at 25° C. for 18 hours during which time a precipitate formed. The reaction mixture was placed directly on 100 ml of silica gel and flash chromotographed using 25% ethyl acetate/hexane to give 1.11 g (1.76 mmol) 88% yield of pure S,S,S,R diester (IIa) (R$_3$,R$_4$=—CH$_2$CH$_2$CH$_2$—, R=CHPh$_2$) as an oil: IR (KBr) 1734, 1657, 1495, 1452, 1185, 1155 cm$^{-1}$; NMR δ1.28(t, 2H, J=7 Hz), 1.7-2.2 (m,6H), 2.43 (m,2H), 2.68 (dd, 1H, J$_a$=17 Hz, J$_b$=13 Hz), 2.80 (m,2H), 3.25 (dd, 1H, J$_a$=17 Hz, J$_b$=6 Hz), 3.46 (t, 1H, J=7 Hz), 4.17 (q, 1H, J=7 Hz), 4.38 (dd, 1H, J$_a$=13 Hz, J$_b$=6 Hz), 5.35 (dd, 1H, J$_a$=6 Hz, J=4 Hz), 5.40 (dd, 1H, J$_a$=6 Hz, J$_b$=2 Hz), 6.25 (s, 1H).

EXAMPLE 6

[4α,7α(R*),12bβ]-7-[[1-{Ethoxycarbonyl}-3-phenylpropyl]amino]-1,2,3,4,6,7,12b-octahydro-6-oxopyrido[2,1-a][2]-benzazepine-4-carboxylic acid (II)

To a stirred solution of 900 mg (1.42 mmol) of (S,S,S,R) benzhydryl ester II from Example 5 (R$_3$,R$_4$=—CH$_2$CH$_2$CH$_2$—, R=CHPh$_2$) and 2.5 ml of anisole at 25° C. under N$_2$ was added 7 ml of trifluoroacetic acid. After stirring for 2 hours, the volatiles were removed in high vacuum to give an oily residue which was dissolved in 4 ml dry ether, stirred vigorously and diluted with hexane. The supernatant was decanted from the gummy solid which was triturated with hexane and vacuum dried to give 750 mg (1.3 mmol) of the tan solid TFA salt of (S,S,S,R) II (R$_3$,R$_4$=—CH$_2$CH$_2$CH$_2$—, R=H) in (91% yield) [α]-$_D{}^{Amb}$=25.5° (c=0.57, CH$_3$OH); IR (KBr) 2300-3400, 1735, 1660, 1195, 1140 cm$^{-1}$; NMR δ(CD$_3$CN,TFA) 1.31 (t, 3H, J=7 Hz), 1.78 (m,2H), 2.3-2.5 (m,4H), 2.84 (m,2H), 3.26 (dd, 1H, J$_a$=17 Hz, J$_b$=13 Hz), 3.68 (dd, 1H, J$_a$=17 Hz, J$_b$=6 Hz), 4.07 (t, 1H, J=6 Hz), 4.29 (m,2H), 5.10 (dd, 1H, J$_a$=6 Hz), J$_b$=2 Hz) 5.20 (dd, 1H, J$_a$=13 Hz, J$_b$=6 Hz), 5.35 (dd, 1H, J$_a$=5 Hz, J$_b$=1 Hz), 7.1-7.4 (m,9H).

Anal. Calcd. for C$_{29}$H$_{33}$F$_3$N$_2$O$_7$: C,60.20; H,5.75; N,4.84. Found: C,60.12; H,5.72; N,4.45.

EXAMPLE 7

[4α,7α(R*),12bβ]-7-[[1-Carboxy-3-phenylpropyl]amino]-1,2,3,4,6,7,12b-octahydro-6-oxopyrido[2,1-a][2]benzazepine-4-carboxylic acid (II)

To a solution of 116 mg (0.20 mmol) of ester II (R=H, R$_3$,R$_4$=—CH$_2$CH$_2$CH$_2$—) from Example 6 in 5 ml 95% ethanol under N$_2$ at 25° C. was added 0.50 ml 1N stock LiOH solution. After stirring for 18 hours, 0.50 ml 1N HCl was added in dropwise fashion with vigorous stirring. The zwitterion was isolated by filtration and vacuum dried to give 80 mg (0.17 mmol) 85% yield of a white solid which was homogeneous by analytical HPLC (Whatman Partisil 10 ODS-3 column, 0.1M ammonium formate buffer in 50% methanol/H$_2$O). Repeated analytical runs on a portion of the sample gave 8 mg of fine colorless crystals from the eluant buffer: mp 259°-260° C.(dec.) [α]$_D{}^{Amb}$=+24° (c=0.05,MeOH); IR(KBr) 1745, 1653, 1630, 1495, 1420, 1305, 1220, 752, 695 cm$^{-1}$; NMR (CD$_3$CN,TFA)δ1.80 (m,4H), 2.3-2.4 (m,2H), 2.9 (m,2H), 3.29 (dd, 1H, J$_a$=17 Hz, J$_b$=13 Hz), 3.70 (dd, 1H, J$_a$=17 Hz, J$_b$=6 Hz), 4.13 (dd, 1H, J$_a$=10 Hz, J$_b$=5 Hz), 5.13 (dd, 1H, J$_a$=6 Hz, J$_b$=2 Hz), 5.24 (dd, 1H, J$_a$=13 Hz, J$_b$=6 Hz), 5.36 (dd, 1H, J$_a$=6 Hz, J$_b$=1 Hz), 7.2-7.4 (m,9H).

Anal. Calcd. For C$_{25}$H$_{28}$N$_2$O$_5$: C,68.79; H,6.46; N,6.42. Found: C,68.49; H,6.53; N,6.50.

EXAMPLE 8

2-Amino-5-heptenoic acid, methyl ester

To a solution of 15.4 ml (110 mmol) of diisopropyl amine in 250 ml dry THF at −78° C. was added 39 ml (105 mmol) 2.7M n-butyl lithium in hexane. After stirring for 30 min., 20 ml hexamethylphosphoric triamide and a solution of 17.7 g (100 mmol) Schiff-base of benzaldehyde and glycine methyl ester in 25 ml tetrahydrofuran were added over 30 min. After an additional 15 min., 13.5 g (100 mmol) 5-bromo-1-pentene was added and the solution was allowed to warm to 25° C. slowly. After 3 hours, the reaction mixture was poured into water and extracted with ether. The extracts were repeatedly washed with brine, then dried over MgSO$_4$ and concentrated to give 25 g of an amber oil. This material was dissolved in 400 ml ether and stirred with 300 ml 0.5N HCl for 2 hours. The aqueous layer was separated and the pH was adjusted to 9 with 1N NaOH. Extraction with chloroform, drying over MgSO$_4$, and concentration gave 4.5 g, as a liquid of the desired compound.

By substituting the 5-bromo-1-pentene with equivalent amounts of 6-bromo-1-hexene or 7-bromo-1-heptene and by following the procedures of this example there are produced the methyl esters of 2-amino-6-octenoic acid and 2-amino-7-nonenoic acid, respectively. (These three compounds correspond to compounds of formula IXb wherein n is 3, 4 or 5, respectively.)

EXAMPLE 9

2-[[2-(1,3-Dihydro-1,3-dioxo-2H-isoindol-2-yl)-1-oxo-3phenylpropyl]

To a solution of 6.0 g (20 mmol) phthalimido-L-phenylalanine and 6.0 g (24 mmol) N-carbethoxy-2-ethoxy-1,2-dihydroquinoline in 30 ml CH$_2$Cl$_2$ was added (21 mmol) of the product from Example 8 in 10 ml CH$_2$Cl$_2$. Gas evolution was observed and stirring was continued for 18 hours. The solution was diluted with CH$_2$Cl$_2$, washed with 10% HCl solution, saturated NaHCO$_3$ solution, and dried over MgSO$_4$. Concentration gave 8.3 g of a yellow oil which was flash chromatographed using 25% ethyl acetate/hexane to give 6.0 g of diastereomeric amide Xb (n=3) as a foam.

Similarly, by substituting 2-amino-5-heptenoic acid methyl ester with equivalent amounts of 2-amino-6-octenoic acid methyl ester or 2-amino-7-nonenoic acid methyl ester and by following the procedure of this example there are produced the corresponding compounds of formula Xb wherein n is 4 and 5, respectively.

EXAMPLE 10

1,2,3,4-Tetrahydro-1-[2-(1,3-dihydro-1,3-dioxo-2H-isoindol-2-yl)-1-oxo-3-phenylpropyl]-pyridine-2-carboxylic acid, methyl ester Olefin from Example 9 (10 mmol) was dissolved in 100 ml CH$_2$Cl$_2$ containing 10 ml absolute methanol and was cooled to −78° C. A stream of ozone in oxygen was passed into the stirred solution until a blue color persisted. After degassing with $N_2$, 10 ml dimethyl sulfide and 0.5 ml pyridine were added and the solution was allowed to warm slowly to 25° C. and stir for 18 hours. The solution was washed with 3 portions 10% HCl solution, dried over $MgSO_4$ and concentrated to give an oil. This crude material was dissolved in 150 ml trichloroethane and treated with 0.5 ml trifluoroacetic acid at reflux for 18 hours. Concentration and flash chromatography gave chromatographically separable diastereomeric acylenamines XIa and XIb (n=3).

EXAMPLE 11

7-(1,3-Dihydro-1,3-dioxo-2H-isoindo-2-yl)-1,2,3,4,6,7,8,12b-octahydro-6-oxopyrido[2,1-a][2]benzazepine-4-carboxylic acid, diphenylmethyl ester The desired acylenamine XIa from Example 10 (1.6 mmol), was dissolved in 5 ml $CH_2Cl_2$ and treated with 2.0 ml trifluoromethane sulfonic acid at 25° C. under $N_2$ for 18 hours. The reaction mixture was partitioned between water and ethyl acetate. The organic extract was washed well with water, concentrated and treated with excess diazodiphenylmethane in $CH_2Cl_2$. Flash chromatography gave cyclized ester XIIa (n=3, R=CHPh$_2$) as a foam.

Analogous chemistry to that described in Examples 8 through 11 gives, when applied to 6-bromo-1-hexene and -7-bromo-1-heptene, homologous tricyclic intermediates XIIa (n=4) and XIIa (n=5), respectively. As described for Example 5, these homologous tricyclic intermediates XII (n=4,5) are deprotected with hydrazine and coupled to an R-triflate of type XXIII to give diesters II ($R_3,R_4$=—$CH_2$—$(CH_2)_2$—$CH_2$—, R=CHPh$_2$) and II ($R_3,R_4$=—$CH_2$—$(CH_2)_3$—$CH_2$—, R=CHPh$_2$), respectively. These diesters are selectively hydrolized as in Example 6 to give the corresponding ester acids (II) (R=H).

EXAMPLE 12

[4R-[4α,7α(S),12bβ]]-7-[(1-Carboxy-3-phenylpropyl)amino]-3,4,6,7,8,12b-hexahydro-6-oxo-1H-[1,4]thiazino[3,4-a][2]-benzazepine-4-carboxylic acid Step A. (R*,R*)-(−)-4-[2-(1,3-Dihydro-1,3-dioxo-2H-isoindol-2-yl)-1-oxo-3-phenylpropyl]-3,4-dihydro-2H-1,4-thiazine-3-carboxylic acid, ethyl ester XVII A 7.75 g (191 mmol) dispersion of 59% sodium hydride/paraffin was washed 2 times with 10 ml dry hexane under a stream of nitrogen. To the purified sodium hydride was added 90 ml anhydrous dimethyl formamide. To this mixture over 20 minutes under a stream of $N_2$ while cooling with an ice/methanol bath was carefully added 17.9 g (96.7 mmol) of the HCl salt of serine ethyl ester. The mixture was allowed to stir 5 min. then 5.2 g (32 mmol) potassium iodide was added. To this mixture was added 14.5 ml (96.7 mmol) bromoacetaldehyde diethyl acetal dropwise over 5 min. The cooling bath was then removed allowing the reaction temperature to rise to 30° C. over the next 10 minutes. The mixture was allowed to stir 8 hrs. at ambient temperature then divided into 2 equal portions, one being added to a solution of 14.2 g (48 mmol) phthalimido-phenylalanine and 11.9 g (48 mmol) N-carbethoxy-2-ethoxy-1,2-di-hydroquinoline in 40 ml dry tetrahydrofuran. The mixture was allowed to stir 18 hours at ambient temperature under $N_2$. The mixture was partitioned between 200 ml $H_2O$ and 200 ml diethyl ether. The phases were separated, and the aqueous portion was extracted with an additional 200 ml ether. The ethereal solutions were combined, successively extracted with (a) 2×200 ml 1N HCl, (b) 2×200 ml saturated $NaHCO_3$, and (c) 50 ml brine. The so-extracted yellow ethereal solution was dried over $MgSO_4$, filtered, concentrated in vacuo, to yield 27.2 g of the expected acetal XVIa (R=$CH_2CH_3$, X=S) as an orange oil. To a solution of 16.1 g (30.3 mmol) of the acetal in 500 ml $CHCl_3$ was added 4.5 ml trifluoroacetic acid. The resultant solution was refluxed 4 hours under an atmosphere of $N_2$, cooled, extracted once with 300 ml saturated $NaHCO_3$, and filtered through anhydrous $MgSO_4$. The resultant solution was concentrated in vacuo to a dark foam which was chromatographed on 500 ml silica gel eluting with 1500 ml 35% ethyl acetate/hexane then with 55% ethyl acetate/hexane. The appropriate fractions were combined then concentrated to give 4.0 g (29%) of the acyleneamine XVII (R=—$CH_2CH_3$, X=S) as a white foam which was crystallized from methanol to give analytically pure product as white needles. Mp 193° C. [α]$_D^{Amb}$= −375.5° (c=0.8,CHCl$_3$), IR(KBr) 3400, 1770, 1740, 1720, 1680, 1620, 1380, 1180, 770, 690 cm$^{-1}$, $^1$H NMR δ(300 MHz); 1.28 (t, 3H, J=7.2 Hz); 3.01 (dd, 1H, $J_a$=13.2 Hz, $J_b$=3.1 Hz): 3.36 (ddd, 1H, $J_a$=13.3 Hz, $J_b$=3.1 Hz, $J_c$=2.4 Hz); 3.48 (d, 1H, J=2.6 Hz): 3.50 (S,1H); 4.23 (q,2H, J=7.3 Hz); 5.19 (dd, 1H, $J_a$=8.6 Hz, $J_b$=2.1 Hz); 5.33 (dd, 1H, $J_a$=8.9 Hz, $J_b$=6.8 Hz); 5.74 (t, 1H, J=3.1 Hz); 5.57 (d, 1H, J=8.6 Hz); 7.15 (s,5H); 7.71 (m,2H); 7.76 (m,2H). $^{13}$C NMR δ(75.4 MHz): 14.1, 26.9, 35.0, 51.0, 53.3, 61.9, 101.9, 119.3, 123.4, 126.7, 128.3, 129.0, 130.9, 134.1, 136.3, 166.3, 166.8, 167.2.

Anal. Calcd. For $C_{24}H_{22}N_2O_5S$: C,63.99%; H,4.92%; N,6.22%. Found: C,64.07%; H,4.97%; N,6.20%.

Step B
[4S-(4α,7α,12bβ)]-7-(1,3-Dihydro-1,3-dioxo-2H-isoindol-2-yl)-3,4,6,7,8,12b-hexahydro-6-oxo-1H-[1,4]thiazino[3,4-a][2]benzazepine-4carboxylic acid, methyl ester XVIII A solution of 0.50 g (1.1 mmol) of the acyleneamine of Step A in 5 ml $CH_2Cl_2$ was added to 1.5 ml $CF_3SO_3H$ under an atmosphere of $N_2$ with stirring. The mixture was stirred at ambient temperature for 18 hours, then poured cautiously into a stirred suspension of excess $NaHCO_3$ in 10 ml methanol. The resultant mixture was concentrated in vacuo partitioned between $CH_2Cl_2$ and $H_2O$ and the aqueous portion extracted with an additional portion of $CH_2Cl_2$. The organic portions were combined, dried over anhydrous $MgSO_4$, concentrated in vacuo to a yellow foam. The foam was dissolved in methanol, allowed to stand overnight at 0° C. The resultant crystals were collected, washed with cold methanol, then dried at about 0.5 mmHg at 60° C. to give 0.35 g (72%) of the expected tricyclic ester XVIII (R=$CH_3$, X=S) as colorless needles, mp 130°–134° C. [α]$_D^{Amb}$= −71.5° (c=0.4, CHCl$_3$). IR(KBr): 3450, 1780, 1730, 1670, 1650, 1380, 1300, 770, 720 cm$^{-1}$.$^1$H NMR δ(300 MHz): 2.93 (dd, 1H, $J_a$=13.6 Hz, $J_b$=3.7 Hz); 3.03 (dd, 1H, $J_a$=14.2 Hz, $J_b$=4.0 Hz); 3.26 (dd 1H $J_a$=16.4 Hz, $J_b$=5.5 Hz); 3.30 (s,3H); 3.38 (ddd, 1H, $J_a$=13.8 Hz, $J_b$=5.8 Hz, $J_c$=1.1 Hz); 50 (dd, 1H, $J_a$=14.0 Hz, $J_b$=6 7 Hz); 4.40 (dd, 1H, $J_a$=16.5 Hz, $J_b$=12.3 Hz); 5.06 (t, 1H, J=4.3 Hz); 5.39 (dd, 1H, $J_a$=6.0 Hz, $J_b$=4.3 Hz); 5.69 (dd, 1H, $J_a$=12.4 Hz); 7.20–7.45(aromatic, 4H); 7.75 (m,2H); 7.88 (m,2H). 13C NMR δ (75.4 MHz, proton decoupled): 27.3, 29.8, 33.9, 351.7, 57.0 (broad), 59.0 (broad), 123.4, 126.6, 127.1, 128.3, 130.2, 133.9, 135.9, 136.0, 167.8, 168.8, 169.2.

Anal. Calcd. for $C_{23}H_{20}N_2O_5S \cdot H_2O$: C,60.78%; H,4.88%; N,6.16%; S,7.05%. Found: C,61.12%; H,4.71%; N,6.10%; S,7.07%.

Step C.
[4R-(4α,7α,12bβ)]-7-Amino-3,4,6,7,8,12b-hexahydro-6-oxo-1H-[1,4]thiazino[3,4-a][2]benzazepine-4-carboxylic acid, methyl ester To a slurry of 0.67 g (1.5 mmol) of the tricyclic ester of Step B in 5 ml methanol was added 3 ml (3.0 mmol) 1N hydrazine hydrate in methanol. The mixture was allowed to stir at ambient temperature under an atmosphere of nitrogen for 60 hours. The mixture was then filtered through Celite with the cake being thoroughly washed with $CH_2Cl_2$. The filtrate was concentrated in vacuo, redissolved in $CH_2Cl_2$, and the organic solution was washed once with $H_2O$ then slowly filtered through $MgSO_4$. The filtrate was concentrated in vacuo to 419 mg of the desired amine as a yellow crystalline solid. An analytical sample was recrystallized from ethyl acetate/hexane to give pure transparent needles mp 143° C. IR(KBr) 3420, 2900, 1730, 1715, 1660, 1430, 1370, 1320, 1300, 1270, 890, 760 cm$^{-1}$. NMR δ(300 MHz, CDCl$_3$)δ1.82 (s,2H), 2.93 (dd, 1H, $J_a$=13.6 Hz, $J_b$=4.8 Hz), 2.97 (dd, 1H, $J_a$=16.2 Hz), $J_b$=13.2 Hz), 3.07 (s,3H), 3.19 (dd, 1H, $J_a$=14.5 Hz, $J_b$=5.0 Hz), 3.31 (ddd, 1H, $J_a$=14.5 Hz, $J_b$=3.8 Hz, $J_c$=2.1 Hz), 3.43 (dd, 1H, $J_a$=14.5 Hz, $J_b$=3.4 Hz), 3.44 (dd, 1H, $J_a$=17.4 Hz, $J_b$=6.2 Hz), 6.50 (dd, 1H, $J_a$=12.8 Hz, $J_b$=6.0 Hz), 5.56 (t, 1H, J=4.4 Hz), 5.62 (dd, 1H, $J_a$=4.6 Hz, $J_b$=2.9 Hz), 7.10-7.25 (complex,3H), 7.37 (m,1H).

Anal. Calcd. for $C_{15}H_{18}N_2O_3S$: C,58.80; H,5.92; N,9.14. Found: C,58.70; H,5.97; N,9.00.

Step D. [4R-[4α,7α(S*),12bβ]]-7-[[1-(Ethoxycarbonyl)-3-phenylpropyl]amino]-3,4,6,7,8,12b-hexahydro-6-oxo-1H-1,4]thiazino[3,4-a][2]benzazepine-4-carboxylic acid, methyl ester To a solution of 374 mg (1.22 mmol) of the amine of Step C and 282 mg (1.34 mmol) 1,8-bis-dimethylaminonaphthelene in 9 ml methylene chloride was added 457 mg (1.34 mmol) of the triflate of Example 5. The mixture was allowed to stir at ambient temperature under an atmosphere of nitrogen for 24 hours after which it was filtered. The filtrate was diluted with 10 ml 50% ethyl acetate/hexane then filtered again. The resultant filtrate was concentrated in vacuo to a dark green glass. The glass was chromatographed on 150 ml silica, eluting with 800 ml 37% ethyl acetate/hexane. Concentration in vacuo and drying yielded 514 mg (84.8%) of the desired diester as a white foam. IR(KBr): 3300, 2950, 2920, 1730, 1650, 1490, 1430, 1320, 1180, 910, 730, 690 cm$^{-1}$. $^1$H NMR δ(300 MHz): 1.22 (t, 3H, J=7.0 Hz); 2.02 (m, 2H); 2.96 (s,3H); 3.18-3.47 (complex,5H); 4.12 (m, 2H); 4.41 (dd, 1H, $J_a$=13.0 Hz, $J_b$=6.0 Hz); 5.46 (t, 1H, J=3.8 Hz); 5.52 (t, 1H, J=3.2 Hz); 7.04-7.30 (aromatic, 9H.) $^{13}$C NMR δ(75.4 MHz, proton decoupled): 14.4, 28.2, 28.4, 32.2, 35.0, 39.0, 50.0, 51.0, 51.9, 55.3, 60.3, 60.9, 125.3, 125.4, 125.9, 127.5, 128.3, 130.3, 134.9, 137.1, 141.1, 169.4, 174.1, 174.9. MS (chemical ionization, methane): MH$^+$=497.3.

Step E. [4R-[4α,7α(S*),12bβ]]-7-[[1-(Ethoxycarbonyl)-3phenylpropyl]amino]-3,4,6,7,8,12b-hexahydro-6-oxo-1H[1,4]thiazino[3,4-a][2]benzazepine-4-carboxylic acid To 766 mg (1.54 mmol) of the diester of Step D was added 2.7 ml (31 mmol) trifluoromethane sulfonic acid at 15° C. The diester dissolved while cooling to 0° C. The dark solution was allowed to stir at 0°-5° C. under an atmosphere of argon for 24 hours then poured cautiously into a solution of 4.03 g (46 mmol) Na$_2$CO$_3$ in 60 ml water. The resultant mixture was extracted with two 30 ml portions of ethyl acetate. The organic portions were discarded. The remaining aqueous solution was acidified to pH=5 with aqueous hydrogen chloride. The resultant turbid mixture was extracted with three 60 ml portions of ethyl acetate. The organic portions were combined then washed with two 30 ml portions of brine. The organic solution was dried over anhydrous magnesium sulfate then concentrated in vacuo to give 288 mg (38%) of a yellow glass, mp 138° C. Analytical data indicate the material to be composed of about 80% of the desired acid ester II ($R_3,R_4$=—$CH_2SCH_2$—, R=H), the major contaminant being the sodium salt of trifluoromethane sulfonic acid. IR(KBr): 3420, 1730, 1650, 1500, 1430, 1250, 1160, 1030, 750, 690, 630 cm$^{-1}$. $^1$H NMR δ(300 MHz, CD$_3$CN): 1.23 (t, 3H, J=7.1 Hz); 2.0 (m, 2H, from CDCl$_3$); 2.70 (t, 2H, J=7.9 Hz); 2.86 (dd, 1H, $J_a$=17.5 Hz, $J_b$=12.2 Hz); 2.95 (dd, 1H, $J_a$=13.7 Hz, $J_b$=4.7 Hz); 3.17 (dd, 1H, $J_a$=14.7 Hz, $J_b$=4.9 Hz); 3.22-3.43 (Complex,4H); 4.12(q,2H, J=7.1 Hz); 4.54 (dd, 1H, Ja=12.9 Hz, $J_b$=5.7 Hz); 5.45 (dd, 1H, $J_a$=4.6 Hz, $J_b$=2.8 Hz); 5.60 (t, 1H, J=4.0 Hz); 7.01-7.36 (aromatic, 9H.)

Step F.
[4R-[4α,7α(S*),12bβ]]-7-[(1-Carboxy-3-phenylpropyl)amino]-3,4,6,7,8,12b-hexahydro-6-oxo-1H-[1,4]thiazino[3,4-a][2]-benzazepine-4-carboxylic acid To a solution of 100 mg (0.2 mmol) of the diester of Step D in 2.27 ml methanol was added 0.5 ml (0.5 mmol) 1N lithium hydroxide. The solution clouded momentarily, but quickly became homogeneous with stirring. The solution was allowed to stir 60 hours at ambient temperature under an atmosphere of nitrogen. The solution was concentrated in vacuo to obtain a white residue. One half of the residue was purified by HPLC on a 25 cm×22 mm ID Partisil 10—ODS3 column with a mobile phase of 0.1M pH=6.2 ammonium formate in 40% methanol-water. The first major peak was collected. The appropriate fractions were combined then concentrated in vacuo. Residual ammonium formate was removed by Kugelrohr distillation at 90° C./1 mm Hg to yield 13 mg (26%) of the desired diacid, mp 232°-235° C. (dec.) IR(KBr): 3420, broad 3100-2200, 1720, 1650, 1630, 1490, 1400, 1200, 750, 690 cm$^{-1}$. $^1$H NMR δ(300 MHz, D$_2$O-TFA): 2.35 (m,2H); 2.89 (td, 2H, $J_a$=10.3 Hz, $J_b$=6.7 Hz); 3.0](dd, 1H, $J_a$=14.0 Hz, $J_b$=4.7 Hz); 3.23 (dd, 1H, $J_a$=15.0 Hz, $J_b$=4.8 Hz); 3.33 (d, 1H, J=2.6 Hz); 3.39 (d, 1H, J=2.6 Hz); 3.42 (dd, 1H, $J_a$=15.0 Hz, $J_b$=5.8 Hz); 3.71 (dd, 1H, $J_a$=16.1 Hz, $J_b$=6.3 Hz); 4.10 (broad s,1H); 5.31 (broad, 1H); 5.48 (d, 1H, J=4.2 Hz); 5.52 (d, 1H, J=4.2 Hz); 7.16-7.38 (aromatic, 8H); 7.49 (d, 1H, J=8.3 Hz); 7.88 (broad d, 2H, J=27.0 Hz).

The preferred diastereomers of these examples may be isolated by conventional means.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases such as, for instance, dicyclohexylamine salts, N-methyl-D-glucamine, salts with amino acids like arginine, lysine and the like. Also salts with organic and inorganic acids can be prepared, utilizing such acids as, for instance, HCl, HBr, $H_2CO_3$, $H_3PO_4$, methanesulfonic, toluenesulfonic, maleic, fumaric, or camphorsulfonic. The non-toxic physiologically acceptable salts are preferred, although other salts are also useful in, for instance, isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying, or by exchanging the cations of an existing salt for another cation on a suitable ion exchange resin The compounds of this invention inhibit angiotensin converting enzyme (hereafter ACE) and thus block conversion of the decapeptide angiotensin I to angiotensin II. Angiotensin II is a potent pressor substance. Thus, blood pressure lowering can result from inhibition of its biosynthesis especially in animals including humans whose hypertension is angiotensin II related. Furthermore, ACE inhibition may lower blood pressure also by potentiation of bradykinin. Although the relative importance of these and other possible mechanisms remains to be established, ACE inhibitors are effective antihypertensive agents in a variety of animal models and are useful clinically in, for example, human patients with renovascular, malignant or essential hypertension. See, e.g., D. W. Cushman, et al., Biochemistry 16, 5484 (1977).

The evaluation of ACE inhibitors is guided by in vitro enzyme inhibition assays. For example, a useful method is that of Y. Piquilloud, A. Reinharz and M. Roth, *Biochem. Biophyc. Acta*, 206 N36 (1970) in which the hydrolysis of carbobenzyloxyphenylalanylhistidinyl-leucine is measured. In vivo evaluations may be made, for example, in normotensive rats challenged with angiotension I by the technique of J. R. Weeks and J. A. Jones, *Proc. Soc. Exp. Biol. Med.*, 104, 646 (1960) or in a high renin rat model such as that of S. Koletsky et al., *Proc. Soc. Exp. Biol. Med.* 125, 96 (1967).

Thus, the compounds of this invention are antihypertensive agents useful in treating hypertensive mammals, including humans, and they can be utilized to achieve the reduction of blood pressure by formulating them in appropriate compositions for administration.

Thus in accordance with the present invention, there is provided a pharmaceutical composition for inhibiting ACE or treating hypertension comprising a pharmaceutically acceptable carrier and a pharmaceutically effective amount of a compound of Formula I.

For administration, the compositions of the invention can also contain other conventional pharmaceutically acceptable compounding ingredients as necessary or desired. Such ingredients are generally referred to as carriers or diluents. Conventional procedures for preparing such compositions in appropriate dosage forms can be utilized. Whatever the dosage form, it will contain a pharmaceutically effective amount of the compound of this invention.

The present compositions can be administered orally or through other means such as, for example, parenterally, topically, rectally, by insufflation, and the like, using appropriate dosage forms such as, for instance, tablets, capsules, suspensions, solutions, and the like, for oral administration; suspension emulsions, and the like, for parenteral administration; solutions for intravenous administration; and ointments, transdermal patches, and the like, for topical administration.

Compositions intended for oral use may be prepared according to any method known to the art for the manufacture of pharmaceutical compositions and such compositions may contain one or more agents selected from the group consisting of sweetening agents, flavoring agents, coloring agents, and preserving agents in order to provide pharmaceutically elegant and palatable preparation. Tablets containing the active ingredient in admixture with non-toxic pharmaceutically acceptable excipients may also be manufactured by known methods. The excipients used may be, for example, (1) inert diluents such as calcium carbonate, sodium carbonate, lactose, calcium phosphate or sodium phosphate; (2) granulating and disintegrating agents such as corn starch, or alginic acid (3) binding agents such as starch, or gelatin or acacia, and (4) lubricating agents such as magnesium stearate, stearic acid or talc. The tablets may be uncoated, or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate, or kaolin. They may also be in the form of soft gelatin capsules wherein the active ingredient is mixed with water or an oil medium, for example, peanut oil, liquid paraffin, or olive oil.

Aqueous suspensions normally contain the active materials in admixture with excipients suitable for the manufacture of aqueous suspensions Such excipients may be, for example:

(1) suspending agents such as sodium carboxymethylcellulose, cellulose, methylcellulose, hydroxypropylmethylcellulose, sodium alginate, polyvinylpyrrolidone, gum tragacanth and gum acacia;

(2) dispersing or wetting agents which may be
  (a) a naturally-occurring phosphatide such as lecithin,
  (b) a condensation product of an alkylene oxide with a fatty acid, for example, polyoxyethylene stearate,
  (c) a condensation product of ethylene oxide with a long chain aliphatic alcohol, for example, heptadecaethyleneoxycetanol,
  (d) a condensation product of ethylene oxide with a partial ester derived from a fatty acid and a hexitol such as polyoxyethylene sorbitol monooleate, or
  (e) a condensation product of an ethylene oxide with a partial ester derived from a fatty acid and a hexitol anhydride, for example, polyoxyethylene sorbitan monoleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin or cetyl alcohol. Sweetening agents and flavoring agents may be added to provide a palatable oral preparation. These compositions may be preserved by the addition of an antioxidant such as ascorbic acid or other suitable preservative.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring, and coloring agents described above, may also be present.

The pharmaceutical compositions of the invention may also be in the form of oil-in-water emulsions. The oily phase may be a vegetable oil such as liquid paraffin or a mixture of vegetable oils. Suitable emulsifying agents may be (1) naturally-occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents such as, for example, glycerol, propylene glycol, sorbitol or sucrose. Such formulations may also contain a demulcent, and preservative and flavoring and coloring agents.

The pharmaceutical compositions may be in the form of a sterile injectable aqueous or oleagenous suspension. This suspension may be formulated according to known methods using suitable dispersing or wetting agents and suspending agents such as those mentioned above. The sterile injectable preparation may also be a sterile injectable solution or suspension in a non-toxic parenterally-acceptable diluent or solvent. Diluents and solvents that may be employed are, for example, water, Ringer's solution, and isotonic sodium chloride solution. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are, for example, cocoa butter and polyethylene glycol.

For topical use, a cream, ointment, jelly, solution, suspension, or the like, which contains a composition of this invention, can be employed.

The amount of active ingredient that may be combined with the carrier materials to produce a single dosage form will vary depending upon the host treated and the particular mode of administration. The compounds of this invention can be administered to patients in need of such treatment in a dosage range of 0.5 to 100 mg active ingredient per patient, generally given several times a day, thus giving a total daily dose of from 0.5 to 400 mg per day. The specific dose level for any particular patient, however, will depend upon a variety of factors including the activity of the specific compound employed, the age, body weight, general health, sex, diet, time of administration, route of administration, rate of excretion, drug combination and the severity of the particular disease undergoing therapy.

The compounds of this invention can also be administered in combination with other antihypertensives and/or diuretics and/or calcium entry blockers. For example, the compounds of this invention can be given in combination with such compounds as acetazolamide, benzthiazide, bumetanide, chlorothalidone, chlorothiazide, clonidine, cryptenamine acetates and cryptenamine tannates, cyclothiazide, deserpidine, diazoxide, diltiazem, (S)-1-[[2-(3,4-dimethoxyphenyl)-ethyl]amino]-3-[4-(2-thienyl)-1H-imidazol-2-yl]phenoxy]-2-propanol, thacrynic acid, flumethiazide, furosemide, guanethidene sulfate, hydralazine hydrochloride, hydrochlorothiazide, hydroflumethiazide, (+)-4-[3-[-[2-(1-hydroxycyclohexyl)ethyl]-4-oxo-2-thiazolidinyl]-propyl]-benzoic acid, indacrinone and variable ratios of its enantiomers, merethoxylline procaine, methylclothiazide, methyldopa, methyldopate hydrochloride, metolazone, metroprolol tartate, minoxidil, naldolol, nifedipine, pargyline hydrochloride, pindolol, polythiazide, prazosin, propanolol, quinethazone, rauwolfia serpentina, rescinnamine, reserpine, sodium ethacrynate, sodium nitroprusside, spironolactone, ticrynafen, timolol, triamterene, trichlormethiazide, trimethophan camsylate, bepridil, diltiazim, etafenone, falipamil, felodipine, flanarizine, gallopamil, indapamide, lidoflazine, nicardipine, nifedipine, nimopidine, nitrendipine, perhexiline, prenylamine, tiapamil, verapamil, and the like, as well as admixtures and combinations thereof.

Typically, the individual daily dosages for these combinations can range from about one fifth of the minimally recommended clinical dosages to the maximum recommended levels for the entities when they are given singly.

To illustrate these combinations, one of the antihypertensives of this invention effective in the 0.5 to 1000 mg per day range can be effectively combined with the following compounds at the indicated per day dose range: hydrochlorothiazide (10–100 mg); chlorothiazide (125–2000 mg); manipulated indacrinone enantiomer ratio (25–150 mg); ethacrynic acid (15–2000 mg); amiloride (5–20 mg); furosemide (5–80 mg); propranolol (20–480 mg); timolol (5–60 mg); and methyldopa (65–2000 mg); and the pivaloyloxyethyl ester of methyldopa (30–1000 mg). In addition, triple drug combinations of hydrochlorothiazide (10–100 mg) plus amiloride (5–20 mg) plus ACE inhibitor of this invention (0.5–1000 mg) or manipulated indacrinone enantiomer ratio (25–150 mg) plus amiloride (5–20 mg) plus ACE inhibitor of this invention (0.5–1000 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

It should be apparent to one of ordinary skill in the art that changes and modifications can be made to this invention without departing from the spirit or scope of the invention.

We claim:

1. A tricyclic lactam having the formula:

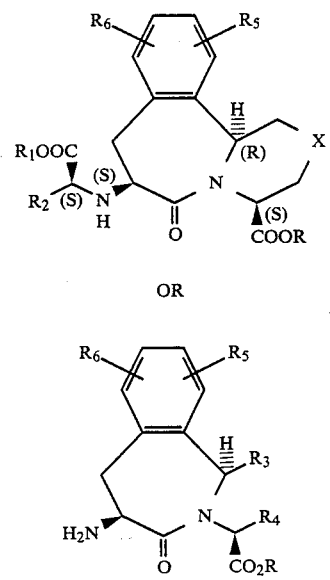

OR

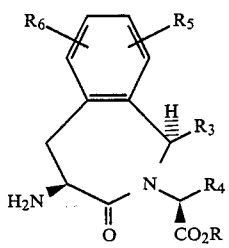

wherein
R and $R_1$ are each hydrogen, methyl or ethyl;
X is S or $CH_2$;
$R_2$ is phenethyl;
$R_3$ and $R_4$ are each H, $C_1$–$C_{12}$ alkyl, phenyl, or benzyl;
$R_5$ and $R_6$ are hydrogen; and the non-toxic physiologically acceptable esters and salts thereof.

2. A compound of claim 1 wherein X is S.

3. A compound of claim 1 wherein X is $CH_2$.

4. A compound of claim 1 wherein R is H, $R_1$ is ethyl, X is $CH_2$, $R_2$ is phenethyl, $R_5$ and $R_6$ are H.

5. A compound of claim 1 wherein R is H, $R_1$ is ethyl, X is S, $R_2$ is phenethyl, and $R_5$ and $R_6$ are H.

6. A compound of claim 1 wherein R and $R_1$ are H, X is $CH_2$, $R_5$ and $R_6$ are H and $R_2$ is phenethyl.

7. A compound of claim 1 wherein R and $R_1$ are ethyl, X is $CH_2$, $R_5$ and $R_6$ are H and $R_2$ is phenethyl.

8. A compound of claim 1 wherein R and $R_1$ are H, X is S, $R_5$ and $R_6$ are H and $R_2$ is phenethyl.

9. A compound of claim 1 wherein R and $R_1$ are ethyl, X is S, $R_5$ and $R_6$ are H and $R_2$ is phenethyl.

10. A process for the preparation of the compounds of claim which comprises:
    (a) coupling a fused lactam having the formula:

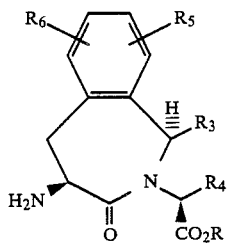

wherein the symbols R, $R_3$, $R_4$, $R_5$ and $R_6$ are as previously described, coupling said lactam with a compound A, B or C having the formula:

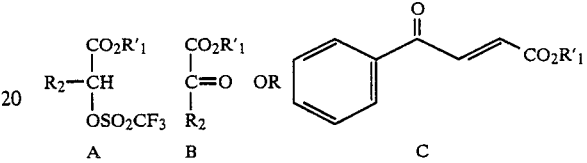

wherein $R'_1$ is methyl or ethyl and $R_2$ is as previously described;
    (b) said coupling with a compound of the type formula A being effected by contacting the reactants together in the presence of a base;
    (c) said coupling with a compound of the type formula B being effected by contracting the reactants together in the presence of a molecular sieve to form a Schiff's base and reducing said Schiff's base;
    (d) said coupling with a compound of the type formula C being effected in accordance with a 1,4-Michael addition reaction followed by a catalytic reduction of the ketone oxygen that is formed; and
    (e) optionally removing one or both of the R and $R'_1$ ester groups.

11. A process according to claim 10 wherein the coupling is effected with a formula A type compound in the presence of a base, such as 1,8-bis-(dimethylamine)-naphthalene.

12. A pharmaceutical composition comprising a compound of claim 2 and a pharmaceutical carrier.

13. A pharmaceutical composition comprising a compound of claim 3 and a pharmaceutical carrier.

14. A pharmaceutical composition comprising the compound of claim 4 and a pharmaceutical carrier.

15. The composition of claim 12 in dosage unit form.

16. The composition of claim 13 in dosage unit form.

17. A method of treating hypertension which comprises administering to a mammal in need thereof an antihypertensive effective amount of a compound of claim 2.

18. A method of treating hypertension which comprises administering to a mammal in need thereof an antihypertensive effective amount of a compound of claim 3.

19. A method of treating hypertension which comprises administering to a mammal in need thereof an antihypertensive effective amount of a compound of claim 5.

20. A method of inhibiting angiotensin converting enzyme (ACE) in a patient in need thereof, which comprises administering to said patient an ACE inhibiting amount of a compound of claim 2.

21. A method of inhibiting angiotension converting enzyme (ACE) in a patient in need thereof, which comprises administering to said patient an ACE inhibiting amount of a compound of claim 3.

* * * * *

UNITED STATES PATENT AND TRADEMARK OFFICE
CERTIFICATE OF CORRECTION

PATENT NO. : 4,973,585

DATED : November 27, 1990

INVENTOR(S) : Gary A. Flynn and Douglas W. Beight

It is certified that error appears in the above-identified patent and that said Letters Patent is hereby corrected as shown below:

Title Page, line 12, "1987," should read -- 1987, abandoned, --.

Column 1, line 9, "14," should read -- filed May 14, --.

Column 1, line 25, add symbol -- $R_3$ -- to the floating bond on the 7-membered ring.

Column 1, line 55, "$C_3C_{10}$cycloalkyl;" should read -- $C_3$-$C_{10}$ cycloalkyl; --.

Column 4, line 64, add -- $\underline{V}$ -- after arrow.

Column 9, line 30, "acetyl" should read -- acetal --.

Column 10, line 16, "-hydroquinone." should read -- -hydroquinoline. --.

Column 10, line 61, "XXIII," should read -- XXII, --.

Column 14, line 54, "Cacd" should read -- Calcd --.

Column 15, line 4, "-phenyl-2trifluorome" should read -- -phenyl-2-trifluorome --.

Column 16, line 42, "3phenylpropyl]" should read -- 3-phenylpropyl]amino]-6-heptenoic acid, methyl ester --.

Column 18, line 40, "-4carboxylic" should read -- -4-carboxylic --.

Column 18, line 48, "in vacuo" should read -- in vacuo, --.

Column 18, line 63, "50" should read -- 3.50 --.

Column 20, line 2, "-3phenylpropyl" should read -- -3-phenylpropyl --.

UNITED STATES PATENT AND TRADEMARK OFFICE
CERTIFICATE OF CORRECTION

PATENT NO. : 4,973,585            Page 2 of 2

DATED : November 27, 1990

INVENTOR(S) : Gary A. Flynn and Douglas W. Beight

It is certified that error appears in the above-identified patent and that said Letters Patent is hereby corrected as shown below:

Column 20, line 5, "-1H[1,4]" should read -- -1H-[1,4] --.

Column 20, line 59, "3.0]" should read -- 3.01 --.

Column 21, line 44, "Biophyc." should read -- Biophys. --.

Column 22, line 51, "cellulose, cellulose," should read -- cellulose, --.

Column 24, line 43, "flanarizine," should read -- flunarizine, --.

Column 25, line 66, "of claim which" should read -- of claim 1 which --.

Signed and Sealed this

Twenty-ninth Day of September, 1992

Attest:

DOUGLAS B. COMER

*Attesting Officer*      *Acting Commissioner of Patents and Trademarks*